(12) United States Patent
Miller et al.

(10) Patent No.: US 8,153,393 B2
(45) Date of Patent: Apr. 10, 2012

(54) SPIROLACTAM TARGETING COMPOUNDS AND RELATED COMPOUNDS

(75) Inventors: Stephen C. Miller, Cambridge, MA (US); Anjan K. Bhunia, West Bengal (IN)

(73) Assignee: University of Massachusetts, Shrewsbury, MA (US)

( * ) Notice: Subject to any disclaimer, the term of this patent is extended or adjusted under 35 U.S.C. 154(b) by 1045 days.

(21) Appl. No.: 12/040,839

(22) Filed: Feb. 29, 2008

(65) Prior Publication Data
US 2008/0233609 A1 Sep. 25, 2008

Related U.S. Application Data

(60) Provisional application No. 60/904,599, filed on Mar. 2, 2007.

(51) Int. Cl.
*C12Q 1/02* (2006.01)
*C07D 265/38* (2006.01)
*C07D 487/00* (2006.01)
*C07D 311/78* (2006.01)

(52) U.S. Cl. ............ 435/29; 544/75; 544/103; 548/418; 549/382

(58) Field of Classification Search ............... 435/29; 544/75, 103; 548/418; 549/382
See application file for complete search history.

(56) References Cited

U.S. PATENT DOCUMENTS

| | | | |
|---|---|---|---|
| 4,139,390 A | 2/1979 | Rauner et al. | |
| 4,857,438 A | 8/1989 | Loerzer et al. | |
| 5,389,489 A | 2/1995 | Yanagihara et al. | |
| 6,008,378 A | 12/1999 | Tsien et al. | |
| 2005/0176065 A1 | 8/2005 | Hanson | |
| 2005/0250759 A1 | 11/2005 | Marin et al. | |
| 2006/0084176 A1 | 4/2006 | Almog | |
| 2006/0182714 A1 | 8/2006 | Behrens et al. | |
| 2008/0299592 A1 | 12/2008 | Miller | |
| 2010/0297684 A1* | 11/2010 | Miller | 435/29 |

OTHER PUBLICATIONS

Adamczyck et al., Tet. Lett., 41, 2000, 807-809.*
Adamczyck et al., Syn. Comm., 2001, 31(17), 2681-2690.*
Adamczyck et al., Tet. Lett., 41, 2000, 807-809.*
Adams et al., "New Biarsenical Ligands and Tetracysteine Motifs for Protein Labeling In Vitro and In Vivo: Synthesis and Biological Applications," J. Am. Chem. Soc., 124:6063-6076 (2002).
Andresen et al., "Short Tetracysteine Tags to β-Tubulin Demonstrate the Significance of Small Labels for Live Cell Imaging," Mol. Biol. Cell, 15:5616-5622 (2004).
Bhunia et al., "Labeling Tetracysteine-Tagged Proteins with a Splash of Color: A Modular Approach to Bis-Arsenical Fluorophores," Chembiochem, 8:1642-1645 (2007).
Griffin et al., "Specific Covalent Labeling of Recombinant Protein Molecules Inside Live Cells," Science, 281:269-272 (1998).

Hoffmann et al., "A FlAsH-Based FRET Approach to Determine G Protein-Coupled Receptor Activation in Living Cells," J. Nat. Methods, 2:171-176 (2005).
Keppler et al., "A General Method for the Covalent Labeling of Fusion Proteins with Small Molecules in vivo," Nat. Biotechnol., 21:86-89 (2003).
Lata et al., "Specific and Stable Fluorescence Labeling of Histidine-Tagged Proteins for Dissecting Multi-Protein Complex Formation," J. Am. Chem. Soc., 128:2365-2372 (2006).
Fujitani et al., "Binding of Soluble Myelin-Associated Glycoprotein to Specific Gangliosides Induces the Association of $p75^{NTR}$ to Lipid Rafts and Signal Transduction," J. Neurochem., 94:15-21 (2005).
Martin et al., "Mammalian Cell-Based Optimization of the Biarsenical-Binding Tetracysteine Motif for Improved Fluorescence and Affinity," Nature Biology, 23:1308-1314 (2005).
Massoud et al., "Molecular Imaging in Living Subjects: Seeing Fundamental Biological Processes in a New Light," Genes Dev., 17:545-580 (2003).
Miller et al., "In vivo Protein Labeling with Trimethoprim Conjugates: a Flexible Chemical Tag," Nat. Methods, 2:255-257 (2005).
Nakanishi et al., "Imaging of Conformational Changes of Proteins with a New Environment-Sensitive Fluorescent Probe Designed for Site-Specific Labeling of Recombinant Proteins in Live Cells," Anal. Chem. 73:2920-2928 (2001).
Shaner et al., "Improved Monomeric Red, Orange and Yellow Fluorescent Proteins Derived from *Discosoma* sp. Red Fluorescent Protein," Nat. Biotechnol., 22:1567-1572 (2004).
Spagnuolo et al., "Improved Photostable FRET-Competent Biarsenical-Tetracysteine Probes Based on Fluorinated Fluoresceins," J. Am. Chem. Soc., 128:12040-12041 (2006).
Steinmeyer et al., "Improved Fluorescent Proteins for Single-Molecule Research in Molecular Tracking and Co-Localization," J. Fluoresc., 15:707-721 (2005).
Stroffekova et al., "The Protein-Labeling Reagent FLASH-$EDT_2$ Binds Not Only to CCXXCC Motifs but Also Non-Specifically to Endogenous Cysteine-Rich Proteins," Pflugers Arch., 442:859-866 (2001).
Weissleder et al., "Shedding Light onto Live Molecular Targets," Nat. Med., 9:123-128 (2003).
Yeo et al., "Cell-Permeable Small Molecule Probes for Site-Specific Labeling of Proteins," Chem. Commun. (Camb.), 23:2870-2871 (2003).
Ando et al., "An optical marker based on the UV-induced green-to-red photoconversion of a fluorescent protein," Proc. Natl. Acad. Sci. U.S.A., 99:12651-12656 (2002).
Cadierno et al., "Ru(IV)-catalyzed isomerization of allylamines in water: A highly efficient procedure for the deprotection of N-allylic amines," Chem. Commun., 4086-4088 (2005).
Furuta et al., "Brominated 7-hydroxycoumarin-4-ylmethyls: novel photolabile protecting groups with biologically useful cross-sections for two photon photolysis," Proc. Natl. Acad. Sci. USA, 96:1193-1200 (1999).
International Preliminary Report on Patentability, PCT Serial No. PCT/US2008/076268, dated Mar. 16, 2010.
International Search Report, PCT Serial No. PCT/US2008/076268, dated Apr. 3, 2009.
Momotake et al., "The nitrodibenzofuran chromophore: a new caging group for ultra-efficient photolysis in living cells," Nature Methods, 3:35-40 (2006).
Wiedenmann et al., "EosFP, a fluorescent marker protein with UV-inducible green-to-red fluorescence conversion," Proc. Natl. Acad. Sci. U.S.A, 101:15905-15910 (2004).

* cited by examiner

*Primary Examiner* — Susannah Chung
(74) *Attorney, Agent, or Firm* — Fish & Richardson P.C.

(57) ABSTRACT

Spirolactam targeting compounds, related compounds, uses of such compounds, and methods of making such compounds are disclosed.

4 Claims, 12 Drawing Sheets

IV

III

VI

V

FIG. 5
Z—G is, e.g., =
—(CH$_2$)$_n$—Nu
—(CH$_2$)$_n$—PNu
—(CH$_2$)$_n$—NHPG
—(CH$_2$)$_n$—NHBOC
—(CH$_2$)$_2$—NHBOC
n is, e.g., = 1, 2, 3, 4, 5, 6, 7, 8, 9, or 10
N is, e.g., = 5-250
—(CH$_2$)$_q$—El
—(CH$_2$)$_q$—PEI
—(CH$_2$)$_3$—COOH
q is, e.g., = 1, 2, 3, 4, 5, 6, 7, 8, 9, or 10

FIG. 11B ReAsH

FIG. 11A FlAsH

5d
SplAsH-ROX
SPiroLactam ArSenical Hairpin binder

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3, 4
<223> OTHER INFORMATION: Xaa = any amino acid

<400> SEQUENCE: 1

Cys Cys Xaa Xaa Cys Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetically generated peptide
```

```
<400> SEQUENCE: 2

Cys Cys Pro Gly Cys Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 3

Leu Val Pro Gly Thr Ile
1               5
```

SPIROLACTAM TARGETING COMPOUNDS AND RELATED COMPOUNDS

CLAIM OF PRIORITY

This application claims priority under 35 USC §119(e) to U.S. Patent Application Ser. No. 60/904,599, filed on Mar. 2, 2007, the entire contents of which are hereby incorporated by reference.

TECHNICAL FIELD

This invention relates to spirolactam targeting compounds, related compounds, and to uses of the same.

BACKGROUND

Our understanding of protein localization and molecular interactions has been greatly enhanced through the use of fluorescent protein fusions. However, there are situations in which the large size (27 kD) of the fluorescent protein interferes with the physiological role of the protein under study (see, e.g., Andresen et al., Mol. Biol. Cell 2004, 15, 5616-5622, and Hoffmann et. al., J. Nat. Methods 2005, 2, 171-176). Furthermore, the spectral properties of fluorescent proteins are thus far restricted to the visible range (see, e.g., Shaner et al., Nat. Biotechnol. 2004, 22, 1567-1572) and their modest photostability has limited their use in many applications, such as single-molecule studies (see, e.g., Steinmeyer et al., J. Fluoresc. 2005, 15, 707-721).

Recently, a number of protein-based tags have been described that recruit small-molecule fluorophores through non-covalent or covalent interactions, both in vitro and in living cells (see, e.g., Los et al., Journal of Neurochemistry 2005, 94, 15-15, Miller et al., Nat Methods 2005, 2, 255-257, and Keppler et al., Nat. Biotechnol. 2003, 21, 86-89). Although these approaches have enabled the use of fluorophores with improved photophysical properties, these fusion proteins present a similarly large change in the size of the modified protein. On the other hand, strategies that utilize much smaller peptide tags—such as hexahistidine (H6) and tetracysteine (TC) motifs—have the potential to allow labeling with minimal perturbation of the protein itself (see, e.g., Lata et al., J. Am. Chem. Soc. 2006, 128, 2365-2372). Tetracysteine tags can be labeled intracellularly, but have thus far been practically limited to hydroxylated xanthene or phenoxazine dyes (e.g., FlAsH and ReAsH) (see, e.g., Griffin et al., Science 1998, 281, 269-272, Adams et al., J. Am. Chem. Soc. 2002, 124, 6063-6076, and Spagnuolo et al., J. Am. Chem. Soc. 2006, 128, 12040-12041).

The simultaneous structural requirements for both fluorescence and the rigid display of arsenic atoms have limited the range of fluorophores that can be targeted to tetracysteine tags. Although fluorescein and resorufin are compatible, their brightness, pH sensitivity and propensity to photobleach are sub-optimal. On the other hand, rhodamines are aminated xanthenes that are pH-insensitive, bright dyes with excellent photostability. However, bis-arsenical rhodamines have been reported to be non-fluorescent, even when bound to a tetracysteine tag (see, e.g., Adams et al., J. Am. Chem. Soc. 2002, 124, 6063-6076). Thus, the scope of compatible dyes can be both narrow and difficult to predict.

SUMMARY

Spirolactam targeting compounds, related compounds, uses of such compounds, and methods for making such compounds are disclosed. For example, chromophoric spirolactam targeting compounds, which have a non-fluorescent targeting moiety (e.g., a bis-arsenical fragment) and a "handle" that includes a tether and a fluorophore, can be conjugated with proteins having tetracysteine tags. This property can make these chromophoric targeting compounds useful for in vivo imaging, as further described herein.

In one aspect, the invention features compounds represented by Structure I, which is shown below.

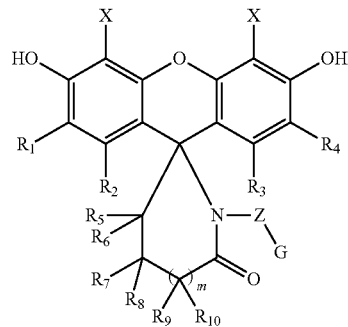

In such compounds, X is independently in each occurrence H, an arsenic-containing moiety, an antimony-containing moiety, or a mercury-containing moiety; $R_1$-$R_{10}$ are each independently H, F, Cl, Br, I, an alkyl group, or an alkoxy group; m is either 0 or 1, corresponding to a 5- or 6-membered ring, respectively; Z is a moiety including up to 25 carbon atoms, optionally including one or more N, O, S, or F atoms, or a polymeric moiety; and G is a fluorophore, a nucleophile, a protected nucleophile, an electrophile, a protected electrophile, a terminal alkyne, or an azide. In such compounds, one of $R_5$ or $R_6$ and one of $R_7$ and $R_8$ can together define a ring and/or one of $R_5$ or $R_6$ and one of $R_7$ and $R_8$ can together define unsaturation. Generally, when X is an arsenic-containing moiety or an antimony-containing moiety, the compounds are considered to be spirolactam targeting compounds. Such spirolactam targeting compounds can have a non-fluorescent targeting moiety (e.g., the bis-arsenical fragment) and a "handle" that includes a tether (Z) and a functionalizable or functionalized group (G). When G is or includes a fluorophore, such targeting compounds are generally referred to herein as chromophoric targeting compounds.

In some embodiments, m is 0, and the compounds are represented by Structure II (shown below).

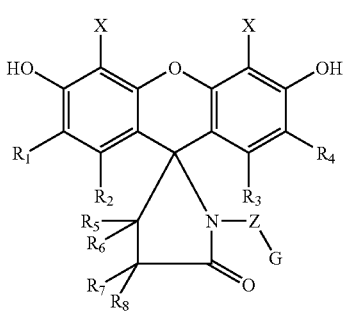

In some embodiments, m is 0, and $R_1$-$R_8$ are each H. In such instances, the compounds are represented by Structure III (shown below).

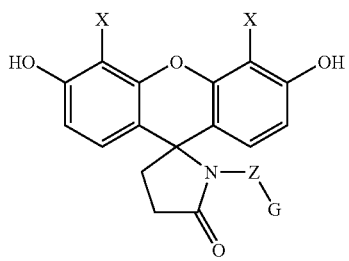

III

In some instances, m is 0, $R_1$-$R_4$ are each H, $R_5$ and $R_7$ together define a ring, and $R_6$ and $R_8$ together define unsaturation. In some instances, such compounds are represented by Structure IV (shown below). While a carbocyclic aromatic ring is shown, heterocyclic rings are possible, such as heterocyclic aromatic rings. While the unsaturation forms part of an aromatic ring, it can form part of a non-aromatic system.

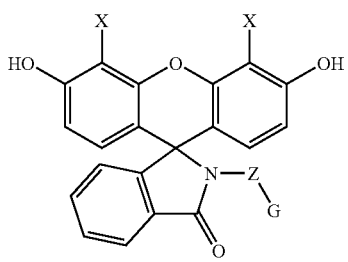

IV

In other instances, m is 1, $R_1$-$R_4$ and $R_9$ and $R_{10}$ are each H, $R_5$ and $R_7$ together define a ring, and $R_6$ and $R_8$ together define unsaturation. In some instances, the compounds are represented by Structure V (shown below). While a carbocyclic aromatic ring is shown, heterocyclic rings are possible, such as heterocyclic aromatic rings. While the unsaturation forms part of an aromatic ring, it can form part of a non-aromatic system.

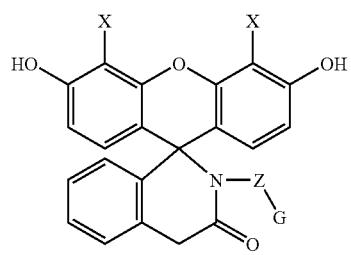

V

In some embodiment, m is 1, and $R_1$-$R_{10}$ are each H. In such embodiments, the compounds are represented by Structure VI (shown below).

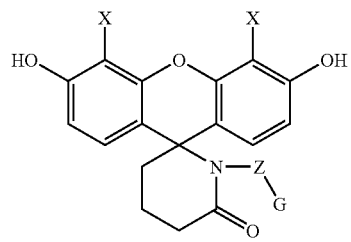

VI

In some embodiments, m is 0, $R_1$-$R_4$ are each H, $R_5$ and $R_7$ together define a ring, $R_6$ and $R_8$ together define unsaturation, and each X is Hg(OAc). In some embodiments, the compounds are represented by Structure VII (shown below). Among other uses, such compounds can be used to form some of the targeting compounds described herein.

VII

In certain implementations, m is 0, $R_1$-$R_4$ are each H, $R_5$ and $R_7$ together define a ring, $R_6$ and $R_8$ together define unsaturation, and each X is As(—$SCH_2CH_2S$—). In some implementations, the compounds can be represented by Structure VIII (shown below). Generally, such compounds are targeting compounds.

VIII

In other implementation, m is 0, $R_1$-$R_4$ are each H, $R_5$ and $R_7$ together define a ring, $R_6$ and $R_8$ together define unsaturation, each X is As(—$SCH_2CH_2S$—), and G is or includes a fluorophore. In some embodiments, such compounds can be represented by Structure XIV. Generally such compounds are chromophoric targeting compounds.

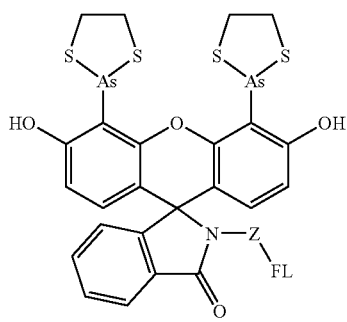

Embodiments can include any one or more of the following features. Z-G is —$(CH_2)_n$-Nu, where n is 1-10, inclusive, and Nu represents a nucleophile; Z-G is $(CH_2)_n$-PNu, where n is 1-10, inclusive and PNu represents a protected nucleophile; Z-G is —$(CH_2)_q$-El, where n is 1-10, inclusive and El represents an electrophile; or Z-G is —$(CH_2)_q$-PEl, where n is 1-10, inclusive and PEl represents a protected electrophile. FL can be, e.g., any one of groups 5a″-5d″ (shown below).

In another aspect, the invention features the compound represented by Structure VII (shown below), where Z-G is $CH_2CH_2NHC(O)$(t-butoxy).

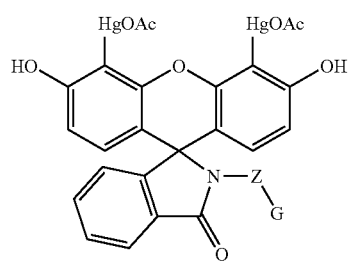

In another aspect, the invention features the compound represented by Structure VIII (shown below), where Z-G is $CH_2CH_2NHC(O)$(t-butoxy). Such compounds represent preferred targeting compounds.

In another aspect, the invention features compounds represented by Structure XIV (shown below).

In such compounds, Z is $CH_2CH_2NH$, and FL is any one of groups 5a″-5d″ (shown below). Such compounds represent preferred chromophoric targeting compounds.

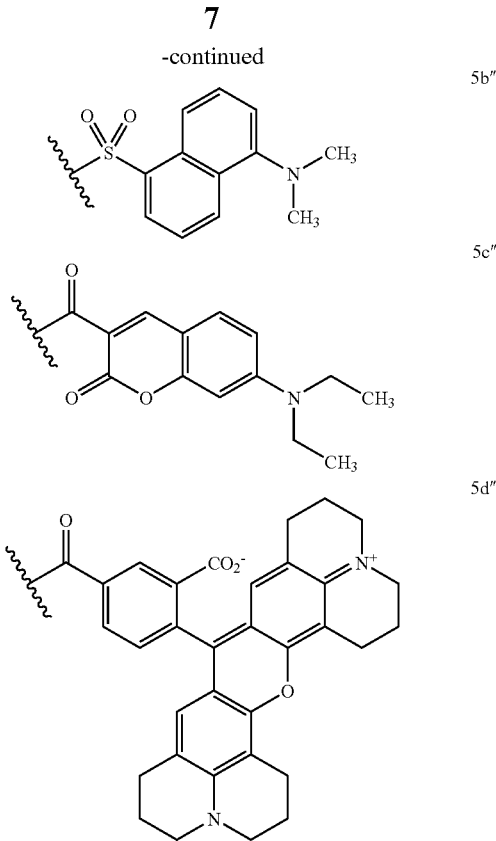

Any of the phenolic compounds described herein can be provided so that one or both phenolic groups are protected with a protecting group, such as an ester. For example, each phenolic group can be acetylated. Once inside cells, the protected phenolic groups would be hydrolyzed to release the phenolic compound. This approach can, e.g., help with cell permeability.

Any of the phenolic compounds described herein can also be provided in salt form. In such implementations, the phenoxide groups can have, e.g., a sodium, potassium, lithium, or calcium ion as counterion.

In another aspect, the invention features conjugates of any of the compounds disclosed herein and a polypeptide (e.g., a peptide or protein).

Embodiments and/or aspects described herein can have one or more of the following advantages. The spirolactam targeting compounds and related compounds can be relatively inexpensive to prepare. The targeting compounds can have a high cell permeability. The targeting compounds can tightly bind to peptides and proteins, such as to those bearing tags, such as tetracysteine tags. The chromophoric targeting compounds can brightly fluorescence. The chromophoric targeting compounds can have any selected emission and/or absorption by selection of the appropriate fluorophore. The fluorophore can absorb and/or emit in the infrared, e.g., near infrared, or visible regions of the electromagnetic spectrum. The targeting moiety can be selected independently of a payload (e.g., a fluorophore). The distance from the targeting moiety and the fluorophore can be pre-determined by selecting an appropriate tether.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference herein in their entirety for all that they contain. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A is a generalized structure for both 5- and 6-membered ring spirolactam compounds (m is 0 and 1, respectively), while

FIG. 4A is a possible generalized structure for 5-membered ring mercury-containing precursors to targeting spirolactams, while

FIG. 5 are possible Z-G moieties.

FIG. 10A shows an image of a gel loaded with tetracysteine-tagged Cdc42 labeled with FlAsH or SplAsH-ROX (5d) as a function of stoichiometry, while

FIG. 11A shows the structure of FlAsH, FIG. 11B shows the structure of ReAsH and FIG. 11C shows the structure of novel SplAsH-ROX.

DETAILED DESCRIPTION

Figure 1B:
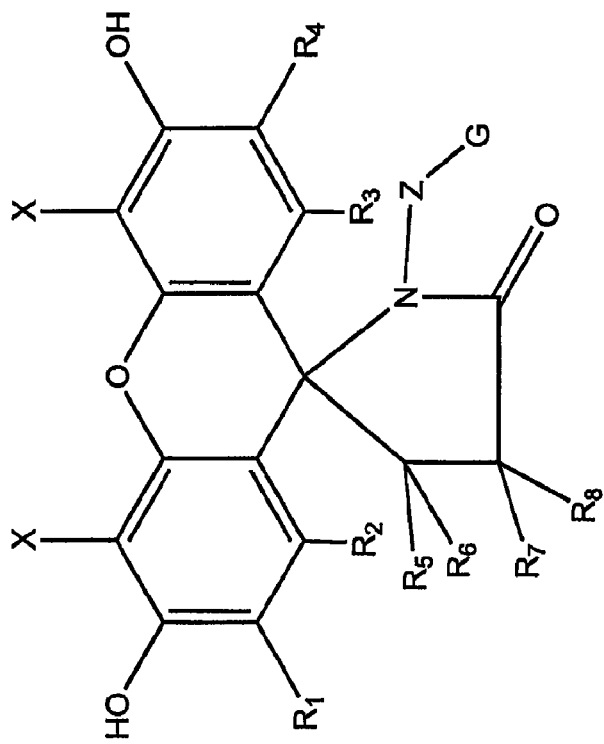
FIG. 1B is a generalized structure for 5-membered ring spirolactam compounds.

Described herein is a general approach that allows for the preparation of a desired spirolactam targeting compound (e.g., a chromophoric spirolactam targeting compound) having desired binding properties. Our novel approach allows for the preparation of the desired targeting compound by independently selecting its non-fluorescent targeting moiety (e.g., a bis-arsenical fragment), its tether, and its payload parts. For example, by decoupling the selection of the parts of the chromophoric spirolactam targeting compound, our approach allows any fluorophore (the payload) to be conjugated with a protein having an appropriate tag, such a tetracysteine tag. The payload could also be a non-fluorescent chromophore, such as a quencher (e.g., QSY-7, QSY-9 and QSY-21 available from Invitrogen Corporation), a "caged" fluorophore that only becomes fluorescent upon illumination with long-wave UV light (e.g., a photocaged fluorescein) or enzymatic activity (e.g., a diacetylated fluorescein), or a polymeric support (e.g., for purification of tetracysteine-containing proteins). For example, the polymer support can be a crosslinked resin, e.g., styrene-divinylbenzene copolymer, support in a chromatography column.

Spirolactam Targeting Compounds and Related Compounds

Generally, compounds represented by Structure I (shown in FIG. 1A) are provided. In such compounds, X is independently in each occurrence H, an arsenic-containing moiety, an antimony-containing moiety, or a mercury-containing moiety; $R_1$-$R_{10}$ are each independently H, F, Cl, Br, I, an alkyl group or an alkoxy group; m is either 0 or 1, corresponding to a 5- or 6-membered ring, respectively; Z is a moiety including up to 25 carbon atoms, optionally including one or more N, O, S, or F atoms, or a polymeric moiety; and G is a fluorophore (e.g., a active or caged fluorophore), a nucleophile, a protected nucleophile, an electrophile, a protected electrophile, a terminal alkyne or azide. In such compounds, one of $R_5$ or $R_6$, and one of $R_7$ and $R_8$ may together define a ring and/or one of $R_5$ or $R_6$ and one of $R_7$ and $R_8$ may together define unsaturation. Generally, when X is an arsenic-containing moiety or an antimony-containing moiety, the compounds are considered spirolactam targeting compounds. Such spirolactam targeting compounds can be viewed as having a non-fluorescent targeting moiety (e.g., a bis-arsenical fragment) and a "handle" that includes a tether (Z) and a functionalizable or functionalized group (G). When G is or includes a fluorophore, such targeting compounds are generally referred to as chromophoric targeting compounds.

Examples of possible alkyl groups include straight chain, branched, mono- or polycyclic alkyl groups. Examples of straight chain and branched alkyl groups include methyl, ethyl, propyl, isopropyl, butyl, isobutyl, sec-butyl, t-butyl, amyl, isoamyl, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl and nonyl. Examples of cyclic alkyl groups include cyclopropyl, cyclobutyl, cyclopentyl, cyclohexyl, cycloheptyl, cyclooctyl, cyclononyl, and cyclodecyl.

Examples of possible alkoxy groups include those derived from primary, secondary or tertiary alcohols that include between one carbon and about 12 carbon atoms. Other examples alkoxy groups include those derived from aromatic hydroxy compounds that include up to 20 carbon atoms, such as phenols and naphthols.

When one of $R_5$ or $R_6$ and one of $R_7$ and $R_8$ together define a ring, the ring can be carbocyclic or heterocyclic. The ring can also be aromatic or non-aromatic. For example the ring can be a 5-, 6 or 7-membered ring. When on of $R_5$ or $R_6$ and one of $R_7$ and $R_8$ together define a ring, the ring can be optionally substituted with one or more alkyl groups or alkoxy groups described herein (or others). Also, the ring can be optionally substituted with one or more F, Cl, Br or I. When one of $R_5$ or $R_6$ and one of $R_7$ and $R_8$ together define unsaturation, the unsaturation can be in the form of a carbon-carbon multiple bond, such as a carbon-carbon double bond. The unsaturation can also be part of an aromatic system.

Figure 1A:
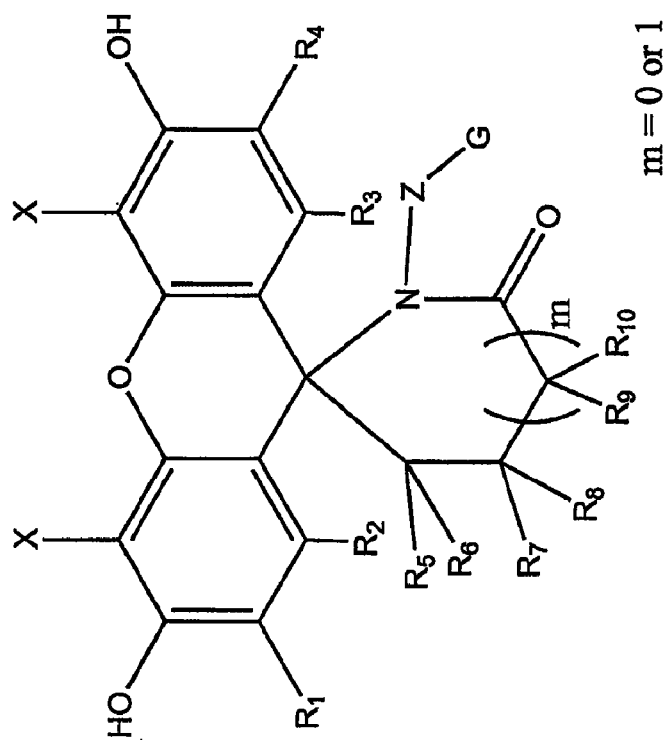

Referring now to FIG. 1B, in some embodiments, m is 0, resulting in compounds which are represented by Structure II. In such embodiments, a 5-membered ring lactam system is provided.

Figure 2B:
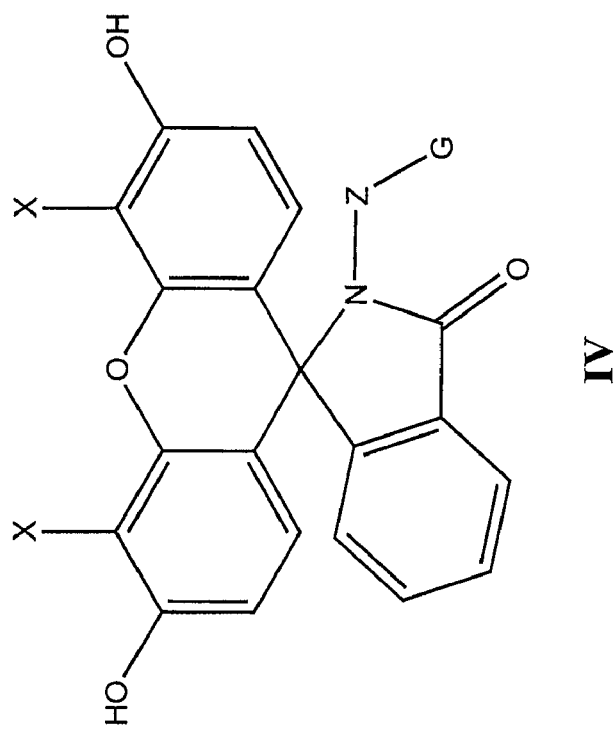
FIGS. 2A and 2B are several possible generalized structures for 5-membered ring spirolactam compounds.
Figure 2A:
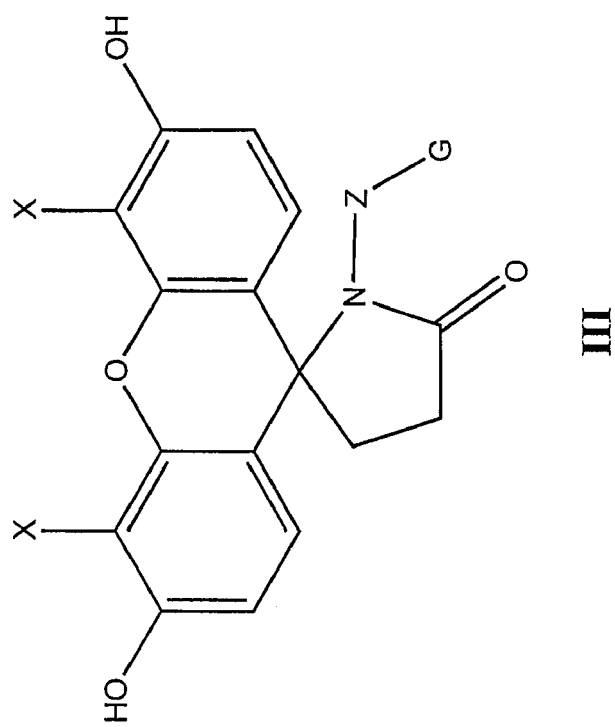

Referring now to FIG. 2A, in some embodiments, m is 0 and $R_1$-$R_8$ are each H. In such instances, the provided compounds are represented by Structure III. Compounds of Structure III include a 5-membered ring lactam system.

Referring now to FIG. 2B, in some instances, m is 0, $R_1$-$R_4$ are each H, $R_5$ and $R_7$ together (along with the lactam ring system) define a 6-membered carbocyclic aromatic ring system and $R_6$ and $R_8$ together form part of the unsaturation in the ring system. In such instances, the compounds are represented by Structure IV. While a carbocyclic aromatic ring is shown (from the combination of $R_5$ and $R_7$), heterocyclic rings can be formed, such as a heterocyclic aromatic ring. While the unsaturation (from the combination of $R_6$ and $R_8$) forms part of an aromatic ring, it can form part of a non-aromatic system.

Figure 3B:
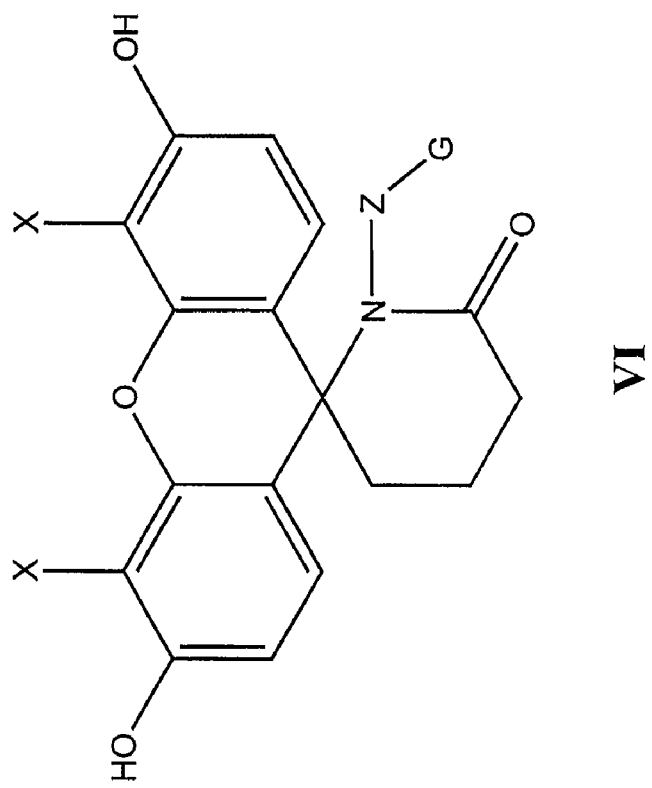
FIGS. 3A and 3B are several possible generalized structures for 6-membered ring spirolactam compounds.
Figure 3A:
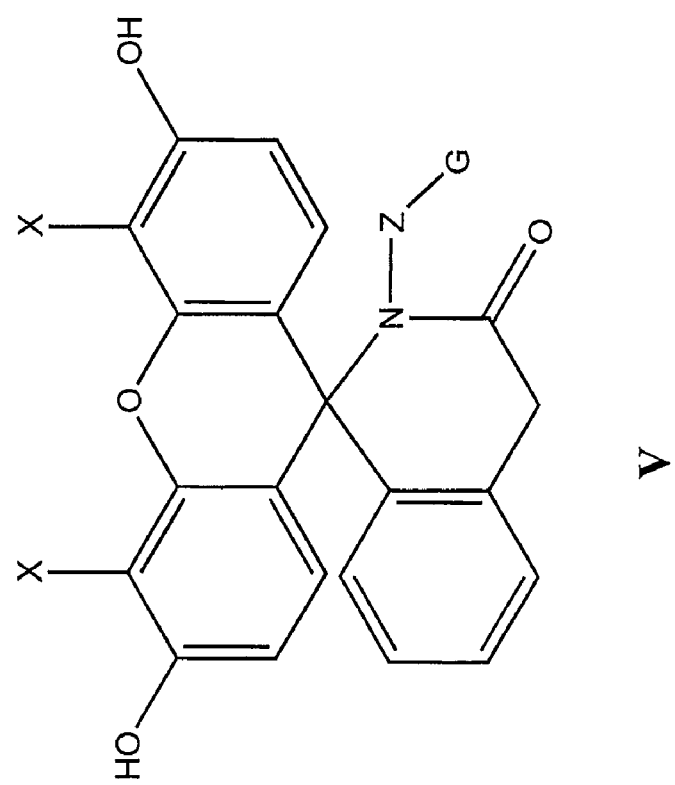

Referring to FIG. 3A, in other instances, m is 1, $R_1$-$R_4$ and $R_9$ and $R_{10}$ are each H, $R_5$ and $R_7$ together (along with the lactam ring system) define a 6-membered carbocyclic aromatic ring system and $R_6$ and $R_8$ together form part of the unsaturation in the ring. In such instances, the compounds are represented by Structure V. While a carbocyclic aromatic ring is shown (from the combination of $R_5$ and $R_7$), heterocyclic rings can be formed, such as a heterocyclic aromatic ring. While the unsaturation (from the combination of $R_6$ and $R_8$) forms part of an aromatic ring, it can form part of a non-aromatic system.

Referring to FIG. 3B, in some embodiments, m is 1 and $R_1$-$R_{10}$ are each H. In such embodiments, the compounds are represented by Structure VI. Compounds of Structure VI include a 6-membered ring lactam system.

Figure 4A:
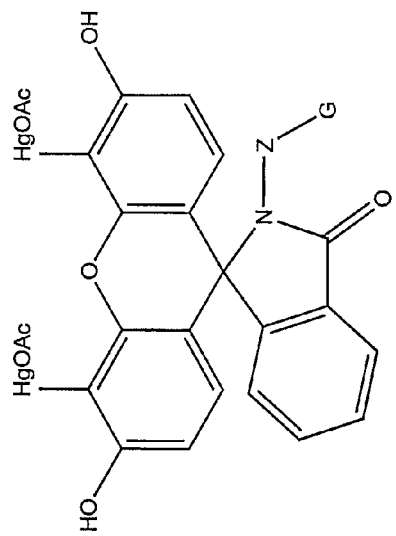

Referring to FIG. 4A, in some embodiments, m is 0, $R_1$-$R_4$ are each H, $R_5$ and $R_7$ together (along with the lactam ring system) define a 6-membered carbocyclic aromatic ring system, $R_6$ and $R_8$ together form part of the unsaturation in the ring system and each X is Hg(OAc). In such embodiments, the compounds are represented by Structure VII. Typically, such compounds can be used to form some of the targeting compounds described herein. While a carbocyclic aromatic ring is shown (from the combination of $R_5$ and $R_7$), heterocyclic rings can be formed, such as a heterocyclic aromatic ring. While the unsaturation (from the combination of $R_6$ and $R_8$) forms part of an aromatic ring, it can form part of a non-aromatic system. Examples of other mercury-containing moieties include Hg(trifluoroacetate).

Figure 4C:
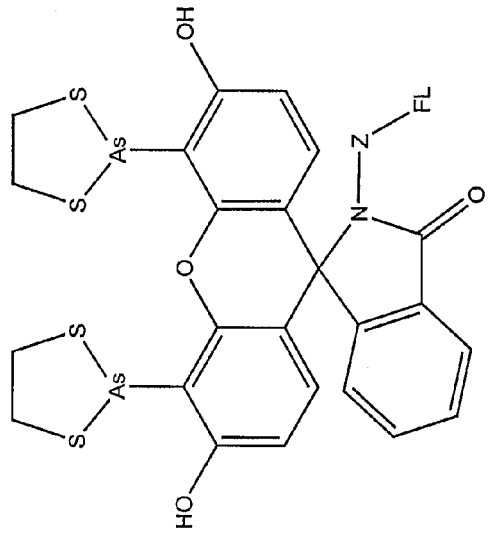
FIGS. 4B and 4C are possible generalized structures for 5-membered ring targeting spirolactams.
Figure 4B:
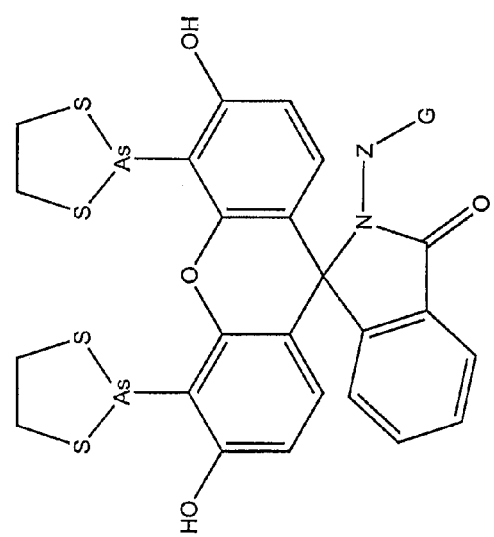

Referring to FIG. 4B, in certain implementations, m is 0, $R_1$-$R_4$ are each H, $R_5$ and $R_7$ together (along with the lactam ring system) define a 6-member carbocyclic aromatic ring system, $R_6$ and $R_8$ together form part of the unsaturation in the ring system each X is As(—SCH$_2$CH$_2$S—). In such implementations, the compounds are represented by Structure VIII. Generally, such compounds represent a class of targeting compounds and can be generally prepared by the corresponding mercury-containing compounds, as will be described below. While a carbocyclic aromatic ring is shown (from the combination of $R_5$ and $R_7$), heterocyclic rings can be formed, such as a heterocyclic aromatic ring. While the unsaturation (from the combination of $R_6$ and $R_8$) forms part of an aromatic ring, it can form part of a non-aromatic system. Examples of other ligands about arsenic include any ligand derived from any dithiol that can form a 5- or 6-membered ring, such as 1,2-benzenedithiol, 1,3-propanedithiol, 2,3-dimercaptosuccinate, and reduced lipoic acid.

Referring to FIG. 4C, in some implementations, m is 0, $R_1$-$R_4$ are each H, $R_5$ and $R_7$ together (along with the lactam ring system) define a 6-member carbocyclic aromatic ring system, $R_6$ and $R_8$ together form part of the unsaturation in the ring system, X is As(—SCH$_2$CH$_2$S—) and G is or includes a fluorophore. In such implementations, the compounds provided are represented by Structure XIV. Generally, such compounds represent preferred class of chromophoric targeting compounds. While a carbocyclic aromatic ring is shown (from the combination of $R_5$ and $R_7$), heterocyclic rings can be formed, such as a heterocyclic aromatic ring. While the unsaturation (from the combination of $R_6$ and $R_8$) forms part of an aromatic ring, it can form part of a non-aromatic system.

Referring back now to FIG. 4B and also to FIG. 5, Z-G can be, e.g., —$(CH_2)_n$-Nu, where n is 1-10, inclusive, and Nu represents a nucleophile, —$(CH_2)_n$-PNu, where n is 1-10, inclusive and PNu represents a protected nucleophile. For example, the nucleophile can be an amino group, e.g., a primary amino group, and the protecting group can be a BOC group. Other nucleophiles include hydroxyl groups and thiol groups. Z-G can also be, e.g., —$(CH_2)_q$-El, where n is 1-10, inclusive and El represents an electrophile, —$(CH_2)_q$-PEl, where n is 1-10, inclusive and PEl represents a protected electrophile. For example, the electrophile can be a carboxylic acid group, an acid chloride group or an isocyanate group.

In other embodiments, Z-G is polymer fragment, such as polyethylene oxide, e.g., having 5-250 repeat units, or a polypropylene oxide. A water soluble polymer fragment can improve solubility and cell permeability of the compounds. Z-G can represent a crosslinked resin.

In still other embodiments, Z-G includes an alkyne group, such as terminal alkyne, or an azide group. An alkyne group can be conjugated with another compound that includes an azide group by the 1,3-dipolar Huisgen cycloaddition reaction.

In a certain precursor compound, the compound is represented by Structure VII (FIG. 4A) and Z-G is $CH_2CH_2NHC(O)$(t-butoxy).

In a certain targeting compound, the compound is represented by Structure VIII (FIG. 4B) in which Z-G is $CH_2CH_2NHC(O)$(t-butoxy).

Figure 6:
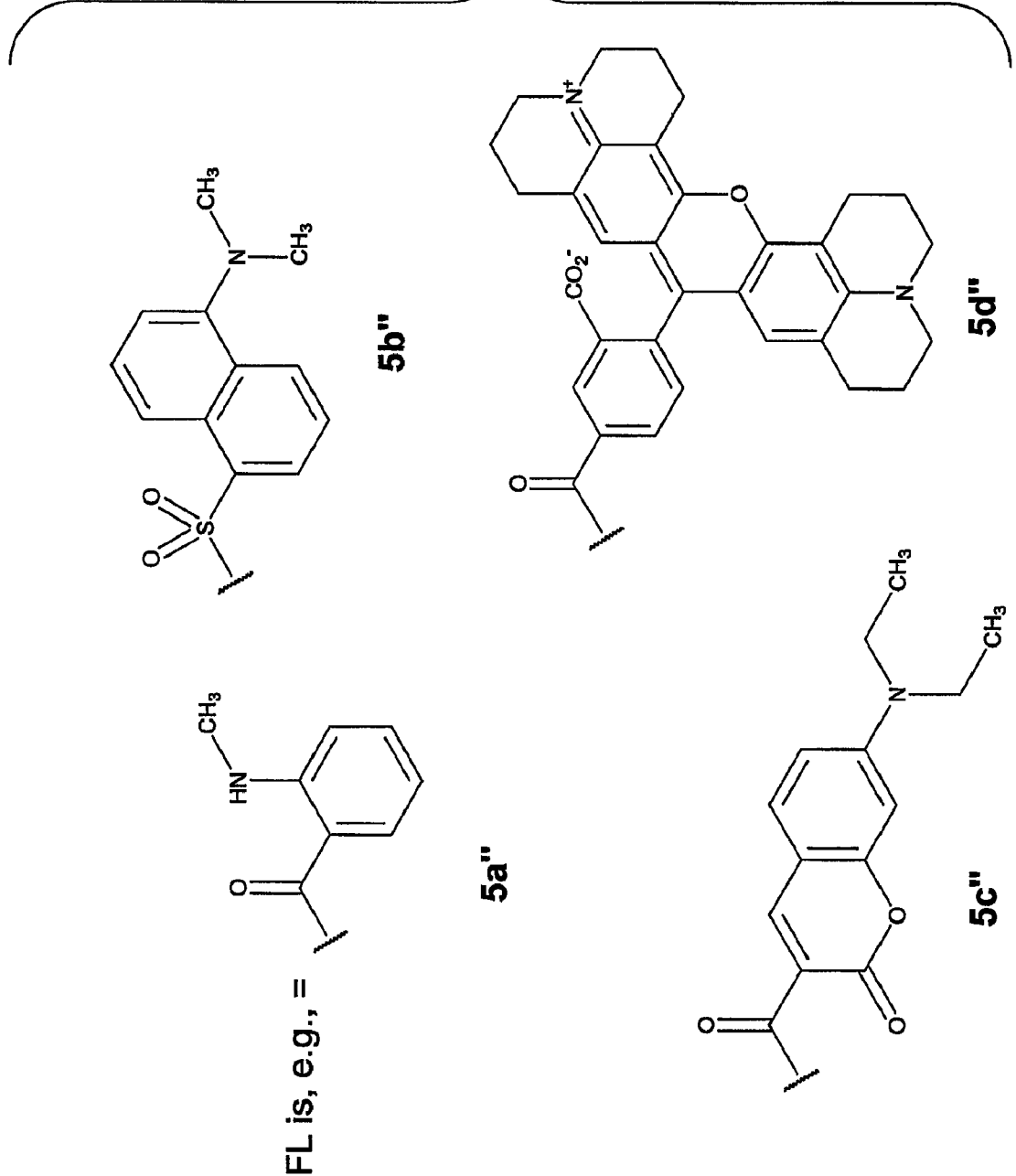
FIG. 6 are possible structures for fluorophores.

Referring back now to FIG. 4C and also to FIG. 6, Z-G can be of the form Z-FL, where FL represents a fluorophore. For example, FL can be any one of groups 5a"-5d" shown in FIG. 6.

Certain chromophoric targeting compounds are represented by Structure XIV (FIG. 4C), in which Z is $CH_2CH_2NH$, and FL is any one of groups 5a"-5d" (FIG. 6).

Synthesis of Spirolactam Targeting Compounds and Related Compounds

Figure 7:
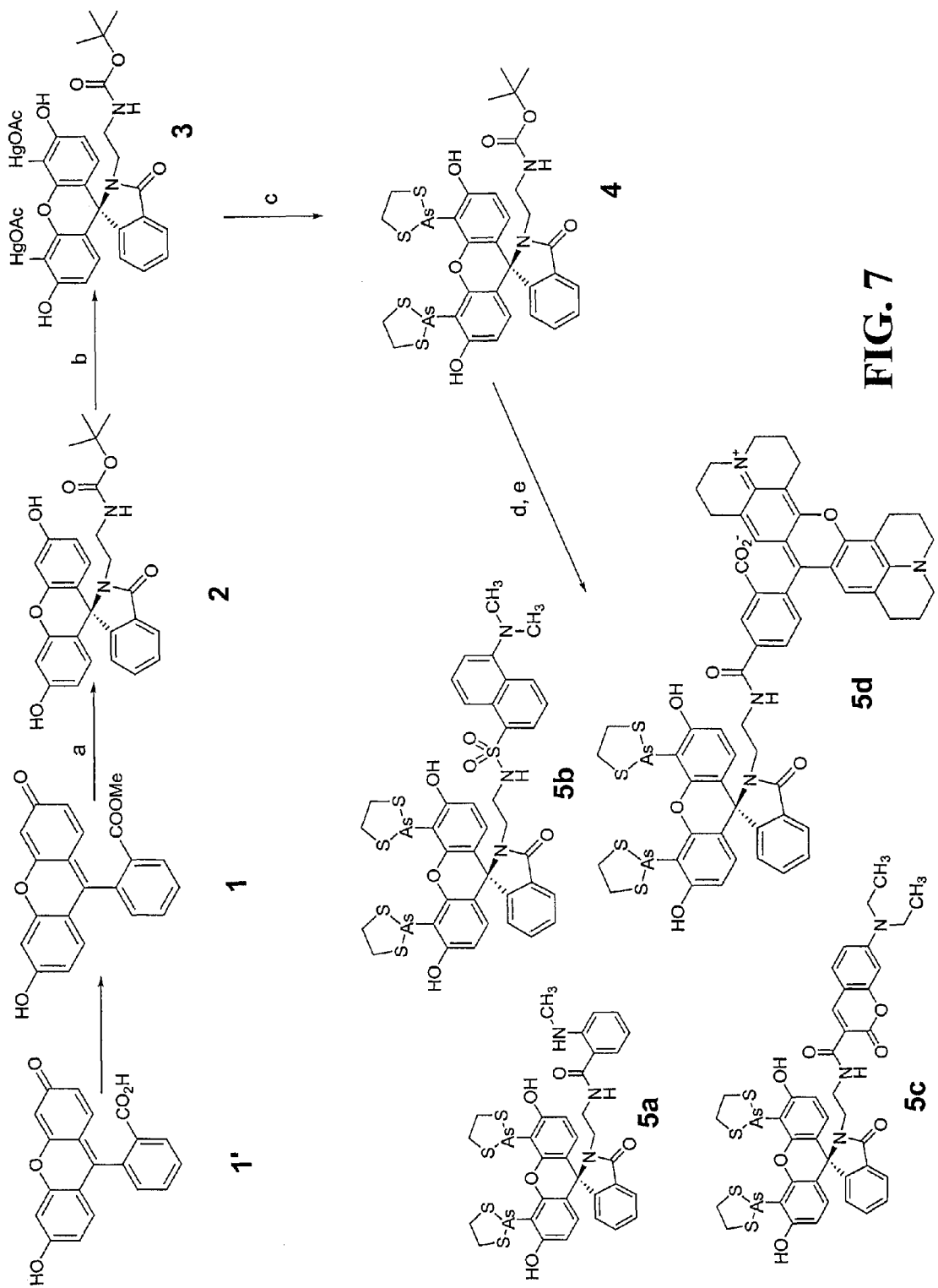
FIG. 7 shows various synthetic schemes for making several spirolactam targeting compounds.
Figure 8:
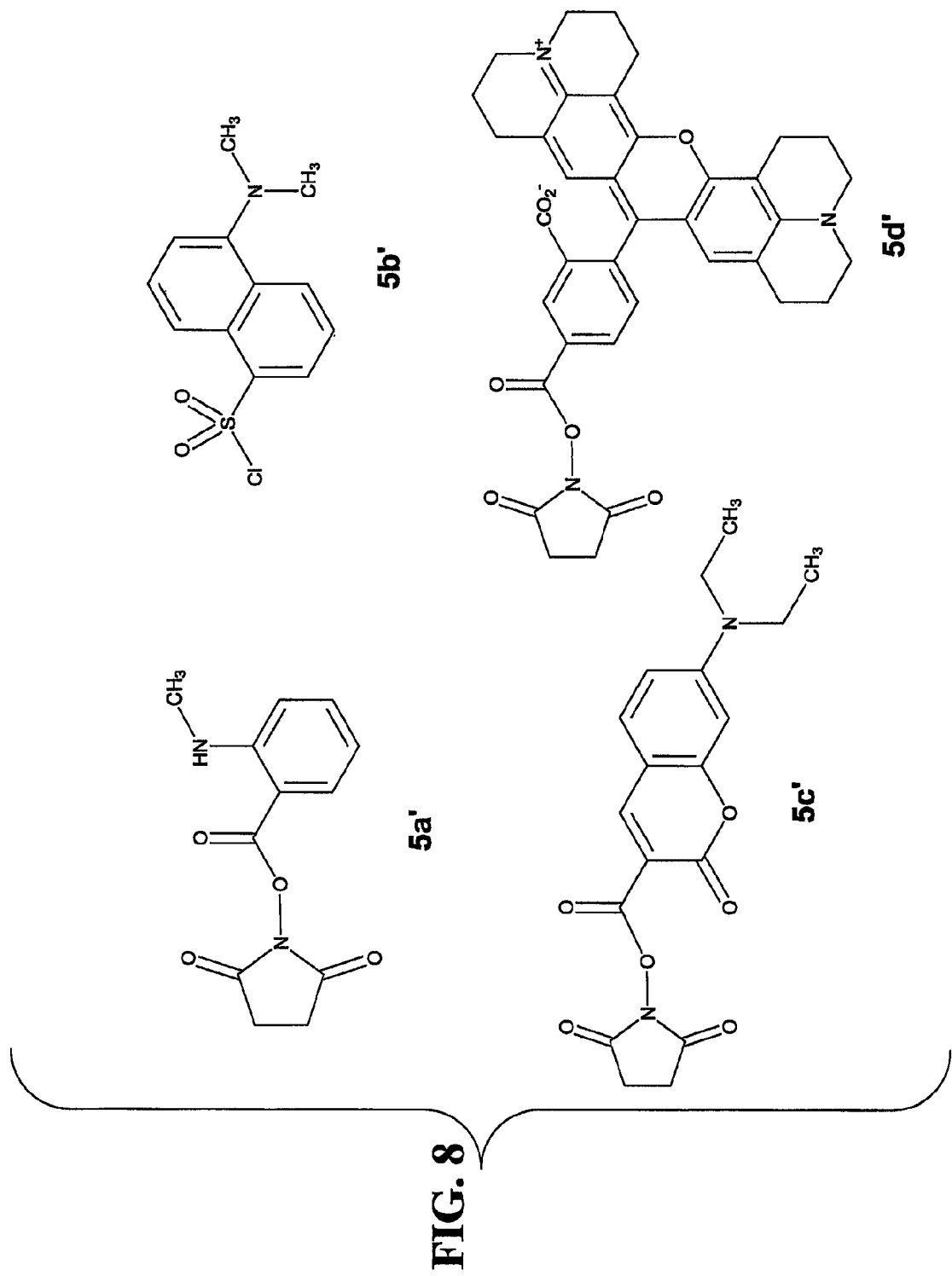
FIG. 8 are various "activated" reactants that can be utilized to give the targeting spirolactams of FIG. 7.

Referring to FIG. 7, chromophoric targeting compounds 5a-5d can be conveniently and relatively inexpensively synthesized from fluorescein (1'). Fluorescein (1') is converted to its methyl ester (1), and then the methyl ester (1) is converted to the 5-membered ring non-fluorophoric spirolactam (2) by treatment with $NH_2(CH_2)_2NHBoc$. Non-fluorophoric spirolactam (2) is converted to the shown corresponding mercury-containing compound (3) by treatment with mercuric acetate in 2% AcOH—$H_2O$. The mercury-containing compound (3) can be converted to the shown arsenic-containing compound (4) by treatment with diisopropylethylamine (DIPEA), arsenic trichloride and $Pd(OAc)_2$, followed by treatment with ethanedithiol. Compounds 5a-5d are prepared by treatment of compound (4) with 30% trifluoroacetic acid (TFA) in dichloromethane to deprotect the compound, followed by treatment of the resulting deprotected bisarsenical compound was reacted with the corresponding dye (as its activated NHS ester or sulfonyl chloride), as shown in FIG. 8 (5a'-5d').

Targeting Tetracysteine Tags with the Spirolactam Targeting Compounds

Figure 9:
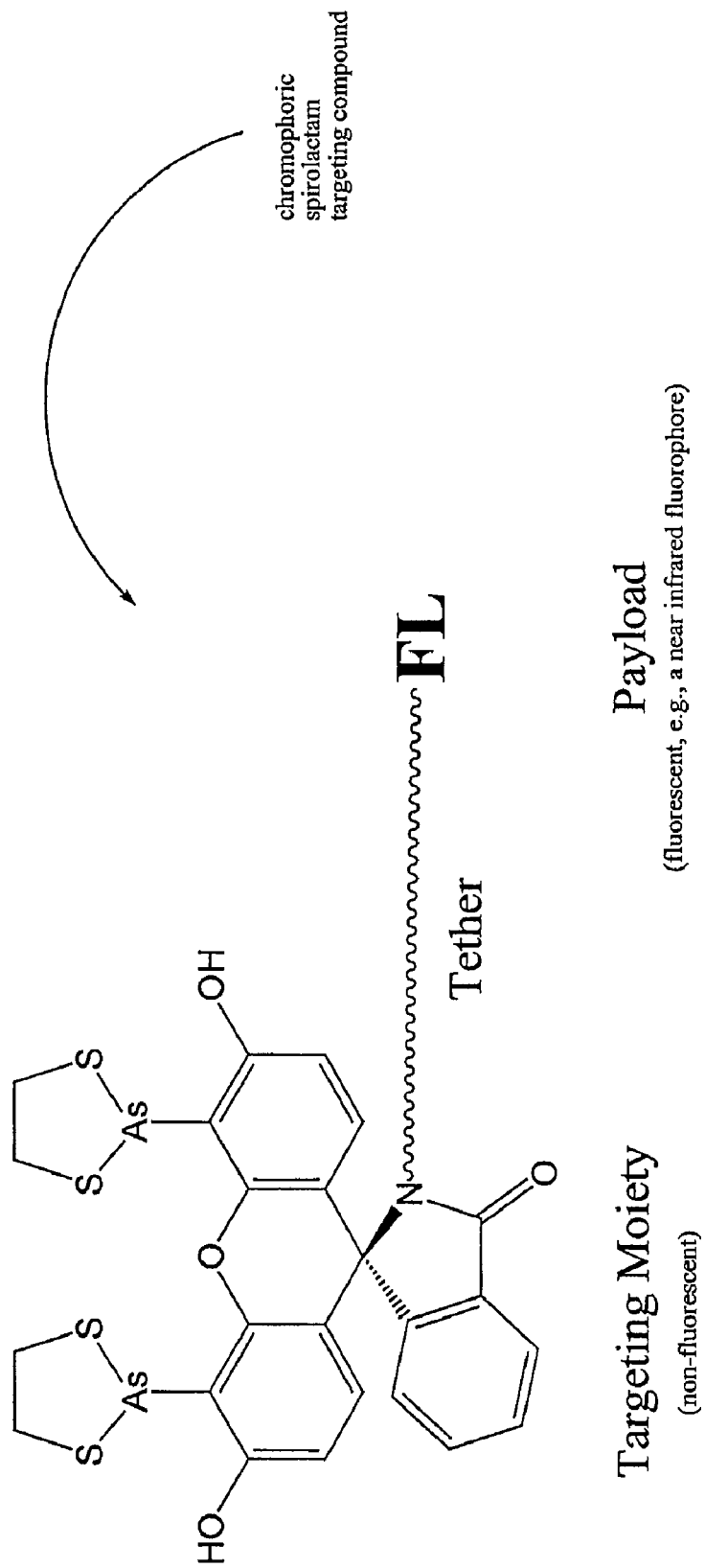
FIG. 9 is a generalized schematic structure of a chromophoric targeting spirolactam.

Referring to FIG. 9, chromophoric spirolactam targeting compounds can be viewed as having a non-fluorescent targeting moiety (e.g., the bis-arsenical fragment) and a "handle" that includes a tether and a fluorophore.

Tetracysteine tags can be conjugated by the targeting compounds described herein, and the chromophoric targeting compounds can be useful for in vivo imaging. The chromophoric targeting compounds are cell-permeable and bind tightly to proteins containing the tetracysteine tag (i.e., CCXXCC (SEQ ID NO:1), in which X is any amino acid, e.g., CCPGCC (SEQ ID NO:2)). For example, modified luciferases that include one or more tetracysteine tags, e.g., linked in tandem at the N or C terminus of the protein, one or more at each terminus, and/or one or more inserted internally into the sequence of the luciferase. For example, residues 35-40 contain a beta-bend (LVPGTI (SEQ ID NO:3)) which could be replaced with CCPGCC (SEQ ID NO:2).

Methods for making tetracysteine-tagged proteins are known in the art (see, e.g., U.S. Pat. App. Pub. No. 2005/0176065 to Hanson et al.). This tag is small and unlikely to perturb protein folding or cellular function. Importantly, the close proximity of the bound fluorophore to the expressed protein is optimal for BRET (bioluminescence resonance energy transfer) applications. BRET is described in RED-SHIFTED LUCIFERASE, which is being filed concurrently herewith Ser. No. 12/040,797.

EXAMPLES

The disclosure is further described in the following examples, which do not limit its scope.

Figure 11C:
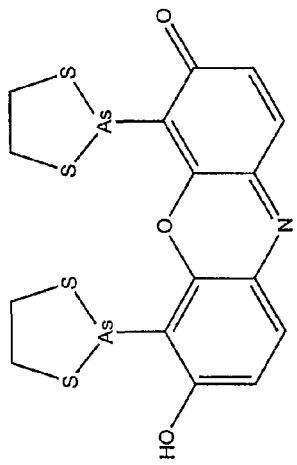
Figure 11C:
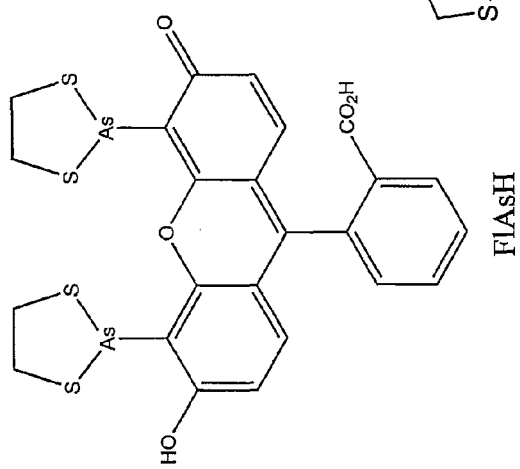
Figure 11C:
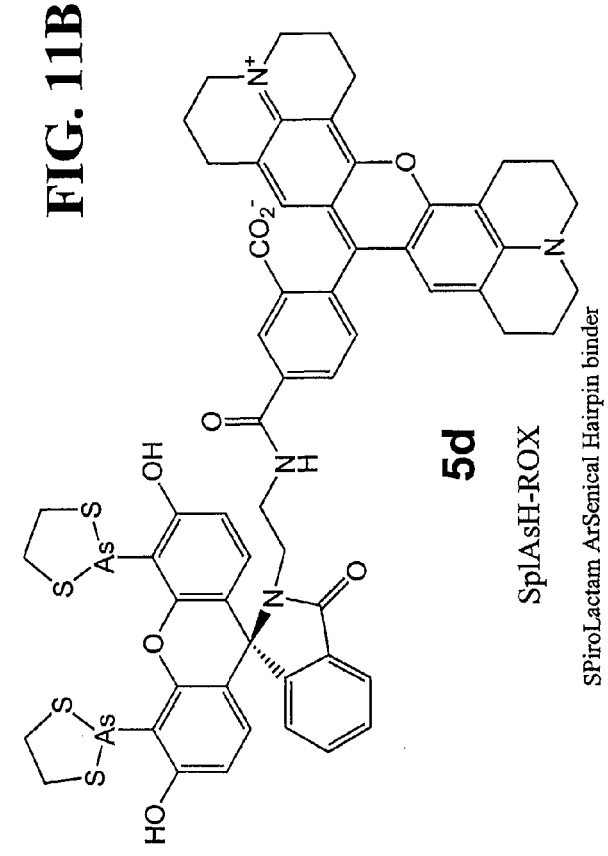

Labeling of Tetracysteine-Tagged Cdc42 with FLAsH and SplAsH-ROX:

Tetracysteine-tagged Cdc42 was labeled with FlAsH, ReAsH or novel SplAsH-ROX (5d) in buffer solution for 30 minutes. The resulting solutions were then placed on SDS-PAGE gels (sodium dodecyl (lauryl) sulfate-polyacrylamide gel electrophoresis) to separate their components. The structures of FlAsH, ReAsH and SplAsH-ROX (5d) are shown in FIGS. 11A, 11B and 11C, respectively.

Figure 10A:
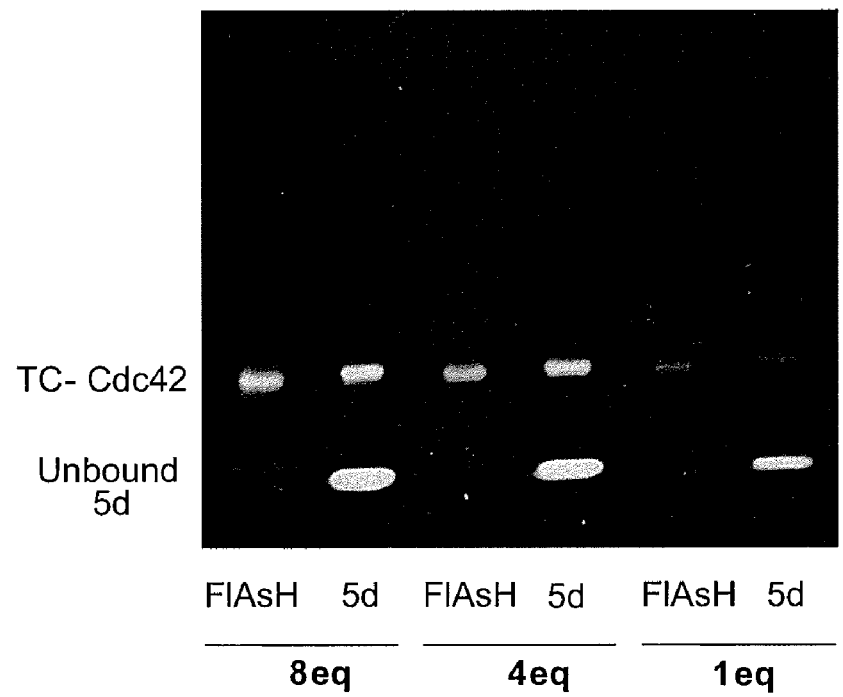
Figure 10B:
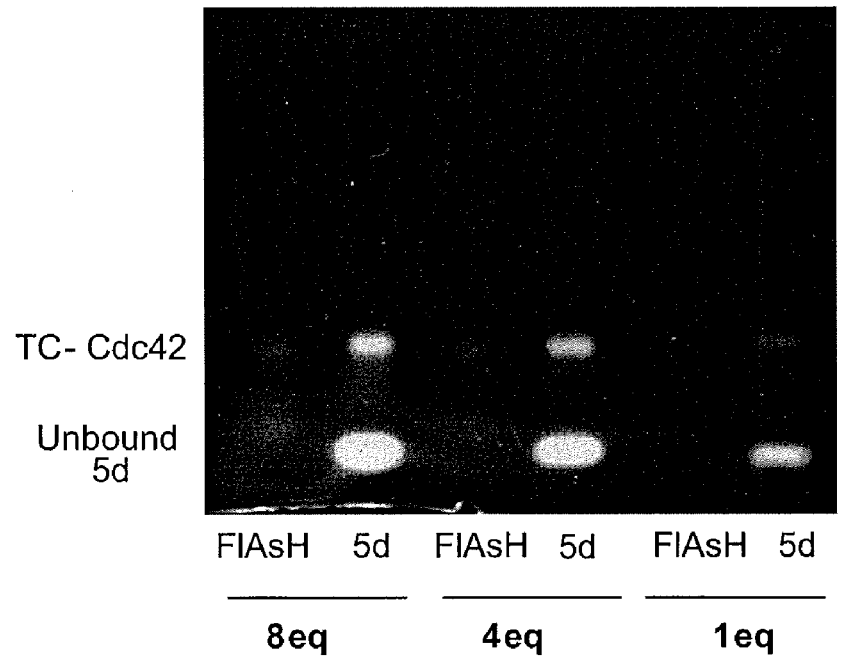
FIG. 10B shows the same gel after irradiation with long-wavelength UV for 2 hours.
Figure 12:
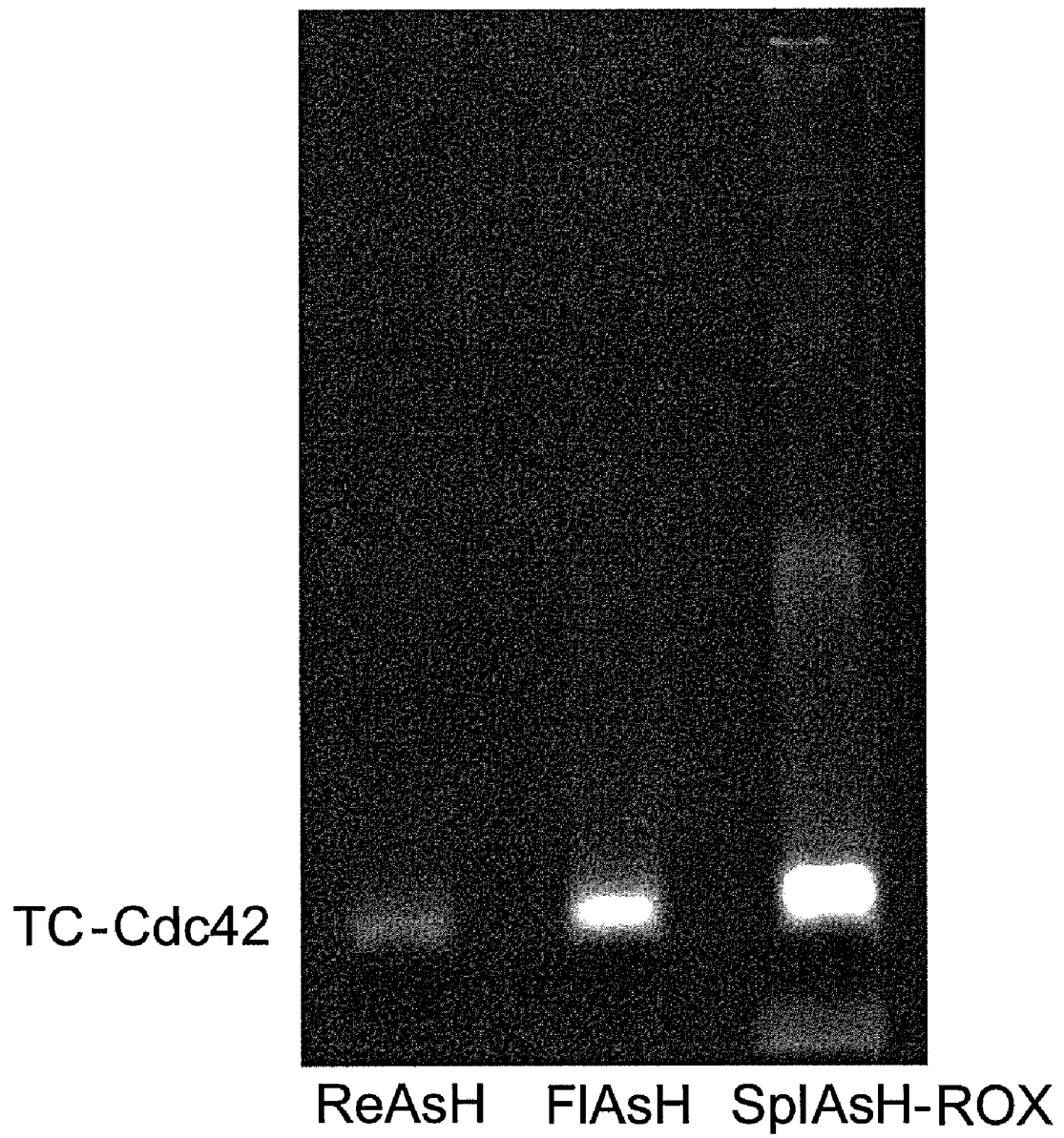
FIG. 12 shows an image of a gel loaded with tetracysteine-tagged Cdc42 labeled with ReAsH, FlAsH or SplAsH-ROX, following removal of unbound dye gel filtration.

FIG. 10A compares labeling intensity as a function of stoichiometry (1 equivalent, 4 equivalents or 8 equivalents) for each of FlAsH and SplAsH-ROX (5d), while FIG. 10B shows the same gel as FIG. 10A after 2 hours of irradiation with a long-wave UV lamp. FIG. 10A shows that Cdc42 labeled with SplAsH-ROX (5d) is brighter than Cdc42 labeled with FlAsH, while FIG. 10b shows that SplAsH-ROX (5d) labeled Cdc42 has a greater photo-stability than Cdc42 labeled with FlAsH. FIG. 12 shows that while the fluorescence of unbound dye is not quenched, any unbound dye migrates with the gel front in SDS-PAGE gels and can be removed by gel filtration. FIG. 12 also illustrates that of the three dyes shown (ReAsH, FlAsH and SplAsH-ROX (5d)), SplAsH-ROX (5d)) labeled Cdc42 is the brightest.

Synthesis of Compound 2: Compound 1 (0.52 g, 1.5 mmol) was dissolved in DMF (5 mL), followed by the addition of $NH_2(CH_2)_2NHBoc$ (0.48 g, 3 mmol). The reaction mixture was heated at 100° C. for 12 h. After cooling, the solvent was evaporated in vacuo and the gummy crude material was purified by flash chromatography. Elution with ethyl acetate: hexanes (50:50, v/v) yielded 0.586 g of white powder. Isolated yield=83%. $^1$H NMR (400 MHz, $CDCl_3$-dmso-d6); 9.0 (s, 2H), 7.87-7.84 (m, 1H), 7.42-7.40 (m, 1H), 6.99-6.96 (m, 1H), 6.63 (d, J=2.1 Hz, 1H), 6.48 (s, 2H), 6.46-6.40 (m, 4H), 3.2 (t, J=5.3 Hz, 2H), 2.88-2.82 (m, 2H), 1.34 (s, 9H). ES-HRMS [M+H]$^+$: 475.1886. Calcd for ($C_{27}H_{26}N_2O_6$): 475.1869.

Synthesis of Compound 3: To a solution of mercuric acetate (701 mg, 2.2 mmol) in 2% AcOH—$H_2O$ (100 mL)

was added an ethanolic solution of compound 2 (0.5 g, 1.05 mmol) at 65° C. The reaction mixture was stirred at 65° C. overnight. The white powder was filtered from the reaction mixture and washed three times with water in order to remove any unreacted mercuric acetate. The dried white solid (0.92 g) was used in the subsequent reaction without further purification. $^1$H NMR indicates complete bis-mercuration of compound 2. Isolated yield=88%. $^1$H NMR (400 MHz, dmso-d$_6$); 7.8-7.78 (m, 1H), 7.5-7.48 (m, 1H), 6.94-6.92 (m, 1H), 6.62 (t, J=4.8 Hz, 1H), 6.54 (d, J=8.4 Hz, 2H), 6.36 (d, J=8.4 Hz, 2H), 3.0 (t, J=6.8 Hz, 2H), 2.71-2.67 (m, 2H), 1.97 (s, 6H), 1.29 (s, 9H).

Synthesis of Compound 4: Compound 3 (0.5 g, 0.5 mmol) was suspended in THF (10 mL). To the suspension was added DIPEA (0.7 mL, 4 mmol), arsenic trichloride (0.8 mL, 10 mmol) and Pd(OAc)$_2$ (5 mg), which resulted complete dissolution of 3 in THF. The reaction mixture was heated to 50° C. for 2 h, then cooled to RT and stirred overnight. The reaction mixture was then poured onto aqueous phosphate buffer (pH 7)-acetone (1:1 v/v 100 mL, 0.5 M K$_2$HPO$_4$) containing ethanedithiol (3 mL). After 30 min of stirring, CHCl$_3$ (50 mL) was added and the mixture was stirred for 30 min. The organic layer was collected and the aqueous layer was washed three times with chloroform (30 mL). The combined organic layer was dried over sodium sulfate and evaporated to dryness. The slightly orange oily residue was purified by flash chromatography. The arsenic-EDT complex was removed by eluting the column with toluene. Further elution with ethyl acetate/hexanes (40:60, v/v) yielded a white powder (0.387 g). Isolated yield=95%. $^1$H NMR (400 MHz, CDCl$_3$); 9.8 (s, 2H), 7.91 (dd, J=2.0 Hz, 6.6 Hz, 1H), 7.51-7.49 (m, 2H), 7.08 (dd, J=1.8 Hz, 6.7 Hz, 1H), 6.49 (d, J=8.7 Hz, 2H), 6.45 (d, J=8.7 Hz, 2H), 3.65-3.5 (m, 8H), 3.2 (t, J=5.8 Hz, 2H), 2.85-2.81 (m, 2H), 1.38 (s, 9H). ES-HRMS [M+H]$^+$: 806.9651. Calcd for (C$_{31}$H$_{33}$As$_2$N$_2$O$_6$S$_4$): 806.9653.

General Procedure for the Synthesis of Compounds 5a-5d: Compound 4 (0.10 g, 0.13 mmol) was treated with 30% TFA in dichloromethane (2 mL TFA in 6 mL dichloromethane) at 0° C. for 3 h. TLC indicated the complete disappearance of the starting material and appearance of a new polar compound. The dichloromethane and TFA was removed in vacuo. The residue was washed three times with saturated sodium carbonate solution and extracted with dichloromethane. The dichloromethane was dried over sodium sulfate followed by the evaporation of the organic solvent, yielding a pinkish solid (64 mg, 91%) which was used in the subsequent reactions without further purification.

The deprotected bisarsenical compound was reacted with the corresponding dye (NHS ester or sulfonyl chloride) in dichloromethane for 3-4 h followed by purification by flash chromatography or preparative TLC.

Compound 5a: Yield=$^1$H NMR (400 MHz, CDCl$_3$); 9.78 (s, 2H), 7.69 (s, 1H), 7.94-7.92 (m, 1H), 7.38 (dd, J=1.5 Hz, 8.1 Hz, 1H), 7.33-7.28 (m, 1H), 7.1-7.08 (m, 1H), 6.65-6.61 (m, 2H), 6.48 (d, J=8.73 Hz, 2H), 6.42 (d, J=8.74 Hz, 2H), 3.67-3.48 (m, 8H), 3.39-3.36 (m, 2H), 3.10-3.06 (m, 2H), 2.84 (s, 3H). ES-HRMS [M+H]$^+$: 839.9675. Calcd for (C$_{34}$H$_{32}$As$_2$N$_3$O$_5$S$_4$): 839.9657.

Compound 5b: $^1$H NMR (400 MHz, CDCl$_3$); 9.76 (s, 1H), 8.5 (d, J=8.6 Hz, 1H), 8.19 (d, J=8.5 Hz, 1H), 7.89 (m, 1H), 7.54-7.44 (m, 4H), 7.06 (d, J=7.2 Hz, 1H), 6.99-6.96 (m, 1H), 6.23 (t, J=5.3 Hz, 1H), 6.18 (d, J=8.7 Hz, 2H), 6.06 (d, J=8.7 Hz, 2H), 3.65-3.50 (m, 8H), 3.15 (t, J=5.3 Hz, 2H), 2.54 (m, 2H), 2.8 (s, 6H). ES-HRMS [M+H]$^+$: 939.9725. Calcd for (C$_{38}$H$_{36}$As$_2$N$_3$O$_6$S$_5$): 939.9640.

Compound 5c: $^1$H NMR (400 MHz, CDCl$_3$); 9.69 (s, 2H), 8.6 (s, 1H), 8.51 (t, J=6.0 Hz, 1H), 7.94-7.91 (m, 1H), 7.47 (dd, J=3.0 Hz, 5.6 Hz, 2H), 7.41 (d, J=8.9 Hz, 1H), 6.53 (d, J=8.7 Hz, 2H), 3.65-3.42 (m, 12H), 3.36 (t, J=6.4 Hz, 2H), 3.21 (m, 2H), 1.23 (t, 6.17 Hz, 6H). ES-HRMS [M+H]$^+$: 950.0024. Calcd for (C$_{40}$H$_{38}$As$_2$N$_3$O$_7$S$_4$): 950.0108

Compound 5d: $^1$H NMR (400 MHz, CDCl$_3$); ES-HRMS [M+H]$^+$: 1223.1263. Calcd for (C$_{59}$H$_{53}$As$_2$N$_4$O$_8$S$_4$): 1223.1178

Other Embodiments

A number of embodiments have been described. Nevertheless, it will be understood that various modifications may be made without departing from the spirit and scope of the invention. Other embodiments are within the scope of the following claims.

What we claim is:

1. A compound represented by Structure XIV:

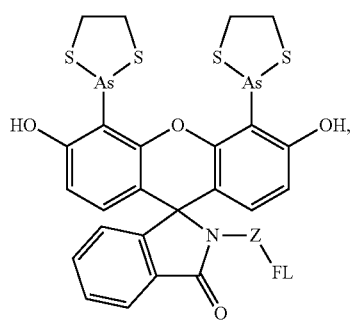

XIV wherein Z is CH₂CH₂NH, and wherein FL is a fluorophore selected from the group consisting of:

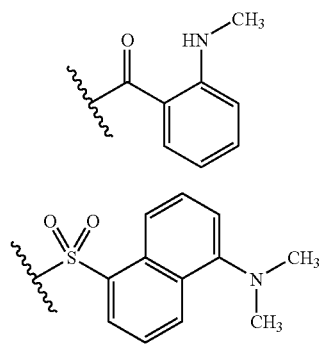

2. A composition comprising a polypeptide having a tetracysteine tag, and the compound of claim 1 conjugated to the polypeptide via the tetracysteine tag.

3. A method of imaging a sample, the method comprising:
providing a sample comprising a polypeptide having a tetracysteine tag;
contacting the sample with a compound of claim 1; and
detecting emission from the compound to image the sample.

4. The method of claim 3, wherein the sample comprises a cell expressing the polypeptide having a tetracysteine tag.

* * * * *